United States Patent
Benbadis et al.

(10) Patent No.: US 6,875,601 B1
(45) Date of Patent: Apr. 5, 2005

(54) **MUTANT *LACTOBACILLUS BULGARICUS* STRAINS FREE FROM β-GALACTOSIDE ACTIVITY**

(75) Inventors: Laurent Benbadis, Anthony (FR); Pierre Brignon, Strasbourg (FR); Francois Gendre, Strasbourg (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 09/700,687

(22) PCT Filed: May 17, 1999

(86) PCT No.: PCT/FR99/01165

§ 371 (c)(1), (2), (4) Date: Feb. 14, 2001

(87) PCT Pub. No.: WO99/61627

PCT Pub. Date: Dec. 2, 1999

(30) Foreign Application Priority Data

May 22, 1998 (FR) .............................. 98 06456

(51) Int. Cl.$^7$ .......................... C12N 1/20; A61K 35/74; A61K 47/00; A23C 9/12
(52) U.S. Cl. ................. 435/252.9; 435/253.4; 424/439; 424/780; 426/42; 426/43
(58) Field of Search .................. 435/252.9, 253.4; 424/439, 780; 426/42, 43

(56) References Cited

U.S. PATENT DOCUMENTS 5,382,438 A * 1/1995 Hottinger et al.
5,639,648 A * 6/1997 Mainzer et al.
5,691,185 A * 11/1997 Dickely et al.

FOREIGN PATENT DOCUMENTS

WO    WO 90 05459 A    5/1990

OTHER PUBLICATIONS

Yoast et al., "Generation and characterization of environmentally sensitive variants of the beta–galactosidase from *L. bulgaricus*", Applied and Environmental Microbiology, 1994, vol. 60, No. 4, p. 1221–1226—abstract.*
Mollet et al., "A beta–galactosidase deletion mutant of *L. bulgaricus* reverts to generate an active enzyme by internal DNA seq duplication", Mol Gen Genet, 1991, 227(1), 17–21—abstract.*

* cited by examiner

Primary Examiner—Leon B. Lankford, Jr.
Assistant Examiner—Ruth A. Davis
(74) Attorney, Agent, or Firm—Alston & Bird LLP

(57) ABSTRACT

The invention concerns mutant *L. bulgaricus* strains bearing a nonsense mutation, in at least one of the sequences coding for the lactose operon, and free from β-galactosidase activity, and lactic starters comprising said strains. Said strains and starters can be used to obtain fermented milk products from glucose-added milk.

9 Claims, 1 Drawing Sheet

MUTANT *LACTOBACILLUS BULGARICUS* STRAINS FREE FROM β-GALACTOSIDE ACTIVITY

These strains and ferments can be used for obtaining fermented dairy products from milk supplemented with glucose.

The present invention relates to novel variants of *bulgaricus* and to their use for preparing fermented dairy products.

Yogurts are conventionally obtained by fermentation of milk with a combination of *Streptococcus thermophilus* and *Lactobacillus bulgaricus*. During the fermentation, which is carried out at a temperature of approximately 40 to 45° C., these bacteria use mainly lactose as an energetic substrate, and produce lactic acid which causes the milk to coagulate; when the pH reaches a value of approximately 4.8 to 4.5, this fermentation step (also named "acidification") is terminated by cooling the product. This product is then kept in the cold during the remainder of the manufacturing and packaging process, and until its consumption.

However, the cooling does not completely stop the lactic acid fermentation; even when the product is kept at 4° C., a gradual increase in its acidity is observed over time.

This phenomenon, known as postacidification, is responsible for degradation of the organoleptic qualities of the product during its conservation.

The postacidification results essentially from the use by the bacteria, and mainly by *L. bulgaricus*, of the lactose remaining in the product at the end of the controlled acidification step. In order to avoid it, it has been proposed to use strains of *L. bulgaricus* which ferment lactose hardly or not at all.

One of the enzymes which are essential for the fermentation of lactose is β-galactosidase, which hydrolyzes lactose into glucose and galactose. It has therefore been proposed, in order to obtain non-postacidifying strains of *L. bulgaricus*, to produce artificial mutants, or to select natural mutants, in which the activity of this enzyme is affected.

For example, patent EP 402 450 in the name of GENENCOR describes the production, by localized mutagenesis of the β-galactosidase gene, of conditional mutants of *L. bulgaricus*, in which the β-galactosidase, which is active during the fermentation at 40° C., loses its activity at the temperature or at the pH corresponding to the conditions of conservation of fermented dairy products.

Application JP 90053437 describes the production of an artificial mutant of *L. bulgaricus* which has completely lost the capacity to ferment lactose, and the selection of a natural mutant with decreased lactose fermentation capacity; these mutants are however both capable of developing and acidifying normally in the presence of *S. thermophilus*, on condition that the medium is supplemented with glucose. The subcultures of these mutants conserve their acidification characteristics, in milk lacking glucose, after 10 subculturings.

Patent EP 0518 096, in the name of the SOCIÉTÉ DES PRODUITS NESTLÉ, proposes to use, for manufacturing yogurt, poorly postacidifying mutants of *Lactobacillus bulgaricus* which have been preselected on the criterion of the deletion of a fragment of the β-galactosidase gene. The screening and characterization of these mutants are facilitated due to the fact that the presence of this deletion can be easily verified on restriction profiles. In addition, the deletions are known to be irreversible mutations, which makes it possible to easily obtain stable mutant strains from the parent strain. Patent EP 0518 096 describes two types of weakly postacidifying mutants selected in this way. The first have a deletion which affects only the β-galactosidase gene; when they are combined with *S. thermophilus* and cultured on milk, they exhibit, even without the addition of glucose, growth and acidification properties which are comparable to those of the wild-type strain from which they are derived. The second have a larger deletion, stretching over at least 1 kb downstream of the β-galactosidase gene; when they are combined with *S. thermophilus*, they grow more slowly and acidify much less than the wild-type strain from which they are derived; the addition of glucose to the culture medium has only a slight influence on their acidification and postacidification properties.

Natural mutants in which the β-galactosidase is inactive are much more difficult to select and to maintain as pure cultures in the case of point mutations than in the case of deletion mutants; this is explained by the lower probability of a point mutation producing an inactive protein, by the greater difficulty in localizing and characterizing the point mutations using restriction profiles, and by the very high reversion rate.

The applicant has now found other natural mutants of *L. bulgaricus*, which do not carry a deletion in the gene encoding β-galactosidase, and which have advantageous technological characteristics. In the context of the present invention, a non-sense mutant, which is incapable of assimilating lactose, has been isolated from a culture of a wild-type *L. bulgaricus*. When combined with *S. thermophilus*, in culture on milk, it grows and acidifies much more slowly than the wild-type strain from which it is derived. Conversely, its growth and its acidification are virtually normal when the milk is supplemented with glucose.

A subject of the present invention is a mutant strain of *L. bulgaricus* lacking β-galactosidase activity, characterized in that it carries a mutation which introduces a non-sense codon into one of the coding sequences of the lactose operon, and in particular the sequence encoding β-galactosidase.

A strain of *L. bulgaricus* in accordance with the invention was deposited according to the Treaty of Budapest, on Jan. 14, 1998, with the CNCM (Collection Nationale de Cultures de Microorganisms [National Collection of Microorganism Cultures]) held by the Pasteur Institute, 25 rue du Docteur Roux, in Paris, under the number I-1968.

This strain has the following morphological and biochemical characteristics:

Morphology: Gram-positive microorganism, immobile, isolated or short-chain, asporogenic, pleomorphic, thin bacilli.

Metabolism: homofermentative, catalase (−).

Fermentation of sugars: D-glucose (+), D-fructose (+), D-mannose (+), esculine (+).

The inventors have sequenced the lactose operon in the I-1968 mutant. The corresponding sequence is represented in the appended sequence listing under the number SEQ ID No: 1. The sequences of the translation products (permease and β-galactosidase) are represented under the numbers SEQ ID No: 2 and SEQ ID No: 3, respectively.

The analysis of this sequence reveals two point mutations: one, in the permease gene (position 122 of the sequence SEQ ID No: 1), induces an amino acid change (Lys→Asn); the other, in the β-galactosidase gene (position 4519 of the sequence SEQ ID No: 1), introduces a stop codon. Although conserving its active sites (positions 464 and 531), the β-galactosidase produced by this mutant is inactive. The inventors have also noted that this mutation remains stable after several series of subculturing, on a culture medium containing glucose. On the other hand, on a culture medium without glucose, this non-sense mutation reverts very rapidly at a rate of approximately $10^{-6}$.

The present invention also encompasses mutant strains which are incapable of assimilating lactose and which are derived from the I-1968 strain. Such strains can, for example, be obtained by inducing other mutations in the lactose operon of the I-1968 strain, by site-directed mutagenesis.

A subject of the present invention is also a lactic ferment, in particular a yogurt ferment, characterized in that it comprises at least one strain of *L. bulgaricus* in accordance with the invention as defined above, preferably combined with at least one strain of *S. thermophilus*.

For the production of a ferment in accordance with the invention, any strain of *S. thermophilus* which is suitable for manufacturing yogurt can be used; the choice of one or more strains of *S. thermophilus* can be made as a function of the additional characteristics that it is desired optionally to confer on the finished product.

By way of example of strains of *S. thermophilus* which can be used in combination with a strain of *L. bulgaricus* in accordance with the invention, mention may be made of the following strains, deposited with the CNCM (Collection Nationale de Cultures de Microorganismes [National Collection of Microorganism Cultures]) held by the Pasteur Institute, 25 rue du Docteur Roux, in Paris:

the strain deposited on Aug. 25, 1994, under the number I-1470, and the strain deposited on Aug. 23, 1995, under the number I-1620; these two strains are described in the European Application published under the number 96/06924;

the strains deposited on Dec. 30, 1994, under the numbers I-1520 and I-1521; these 2 strains are described in PCT international application WO 96/20607;

the strain deposited on Oct. 24, 1995 under the number I-1630; the characteristics of this strain are described in PCT international application WO 96/01701.

These strains can be combined mutually or with one or more other industrial strains of *S. thermophilus*.

The strain(s) of *S. thermophilus* is (are) combined with the strain(s) of *L. bulgaricus* in accordance with the invention, in the same way and in the same proportions as in conventional yogurt ferments; the population of *L. bulgaricus* bacteria in accordance with the invention may, for example, represent between 10 and 90%, preferably between 20 and 50%, of the total bacterial population.

A subject of the present invention is also a method for preparing a fermented dairy product, characterized in that it comprises a step during which milk is fermented using a ferment comprising at least one strain of *L. bulgaricus* in accordance with the invention, in the presence of at least one sugar which can be assimilated by said strain; it can be in particular fructose, mannose and, preferably, glucose. Advantageously, said fermented dairy product is a yogurt.

The method in accordance with the invention is similar to conventional methods for preparing yogurt with regard to the main methods of implementation of the controlled acidification step; in particular, this acidification is carried out at a temperature of between 20 and 45° C., and preferably between 30 and 45° C., and "batchwise", i.e. in a single step and using a single fermentation tank.

The duration of this controlled acidification step is generally about 6 to 24 hours, and preferably about 6 to 16 hours; it is therefore longer than in the case of conventional methods for preparing yogurt (in which it is 3 to 5 hours at 44° C.). Specifically, the strains of *L. bulgaricus* in accordance with the invention, even combined with *S. thermophilus*, grow and acidify much more slowly than the wild-type strains.

In addition, the rate of growth and acidification of the strains of *L. bulgaricus* in accordance with the invention varies very significantly depending on the amount of glucose added to the milk. This property makes it possible to control their growth and their acidification, by simply adding the desired amount of glucose at the start of fermentation.

The inventors have also observed that, when strains of *L. bulgaricus* or ferments in accordance with the invention are used, the acidification slows down considerably when the pH reaches the range of 4.8 to 4.5 (which corresponds to the pH range at which acidification is stopped in the case of a conventional method), and stabilizes, even if the milk is maintained at fermentation temperature, at a minimum pH. The value of this minimum pH depends essentially on the amount of glucose added.

This property makes it possible to reduce, or even to eliminate, the cooling phase used in conventional methods for manufacturing yogurt to stop the fermentation. It also eliminates the necessity of measuring the pH to determine the optimum moment for stopping the fermentation; for a given ferment and amount of added glucose, it is possible, without risk of overacidification, to stop the fermentation at the end of a given period, calculated as a function of the time required to reach the minimum pH. This makes it possible to have better control of the regularity of the final pH and of the texture for the product at the end of fermentation.

Advantageously, for the implementation of the method in accordance with the invention, and depending on the degree of acidification that it is desired to reach, the amount of glucose added to the milk prior to the fermentation is between 0.5 and 10 g/l, preferably between 0.5 and 5 g/l.

The fermented product obtained in this way can be conserved for several hours at a temperature close to the fermentation temperature, without a drop in pH, thereby making it possible to eliminate the installations for intermediate cold storage, and to increase the capacity of the fermentation tanks.

The implementation of the method in accordance with the invention makes it possible to reduce the postacidification in the fermented products during their longer term conservation. The degree of postacidification can vary depending on the composition of the ferment and the amount of glucose used. However, the postacidification is always clearly lower than that observed in the case of yogurts obtained with conventional ferments and methods.

For example, experiments carried out by the inventors have shown that, under the same conservation conditions (28 days of conservation at 10° C.), the ΔpH (difference between the pH at D0 and the pH at D28) is between 0.05 and 0.4 in the case of the products obtained using a ferment in accordance with the invention, whereas it is always greater than 0.7 in the case of control ferments in which the strain of *L. bulgaricus* in accordance with the invention is replaced with a wild-type strain.

This weak postacidification is accompanied by good survival of the strains of the ferment; the population of *L. bulgaricus*, at the end of conservation, in the fermented product obtained in accordance with the invention is only slightly smaller than that of the control product.

A subject of the present invention is also the fermented dairy products which can be obtained by implementing a method in accordance with the invention.

These products can be conserved for a longer time and at higher temperatures than the products obtained using conventional methods, and have organoleptic properties which remain stable during conservation.

EXAMPLE 1

Figure 1:
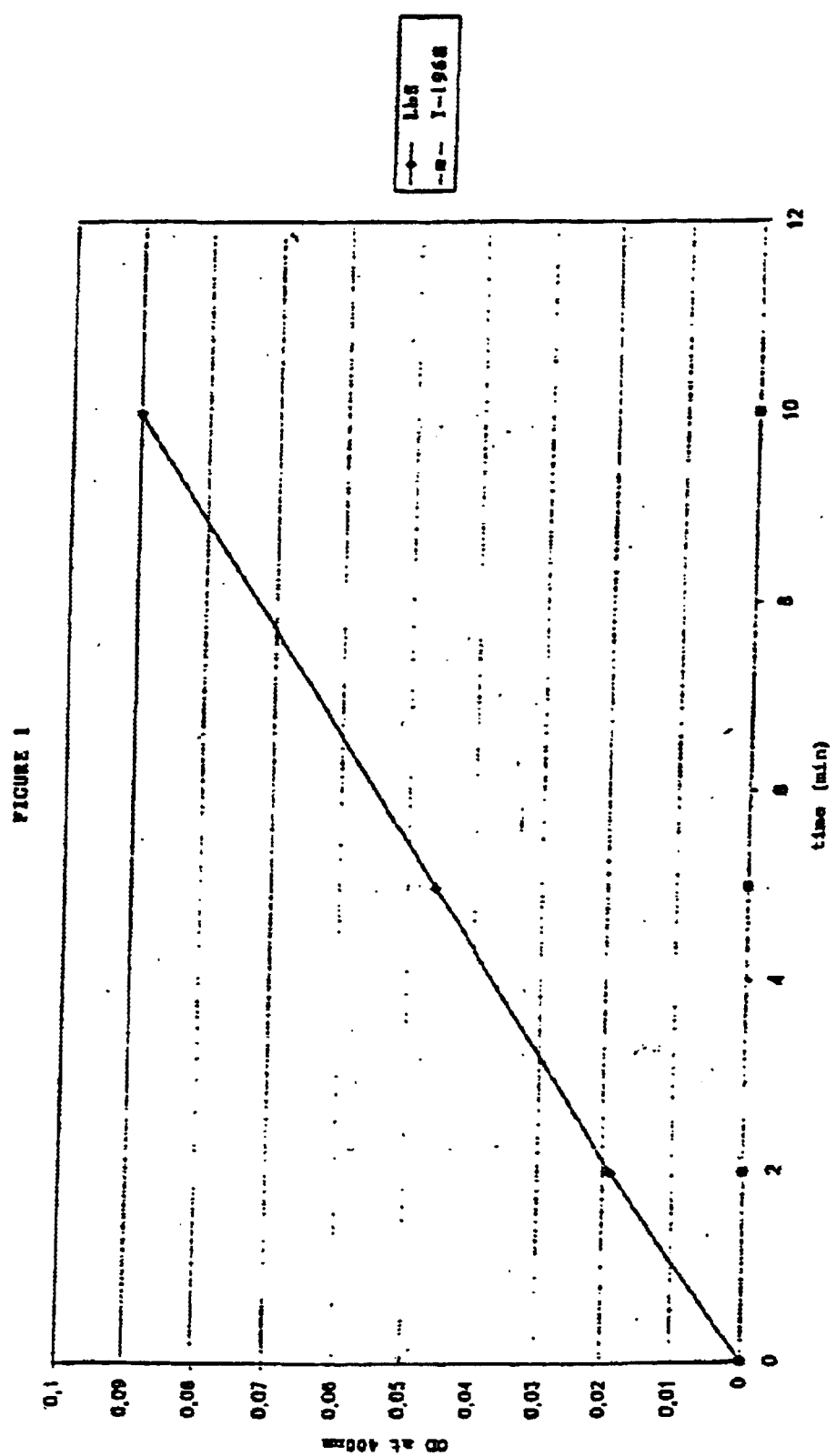
FIG. 1 is a graph showing the galactosidase activities of the LbS parent strain and of the I-1968 mutant in accordance with the invention, measured as a function of time.

Biochemical Assaying of the β-Galactosidase Activity of a Mutant in Accordance with the Invention The β-galactosidase activity of the I-1968 strain was compared with that of the wild-type strain of *L. bulgaricus* (hereafter termed LbS) from which it is derived.

The bacteria are cultured overnight on MRS agar medium (MERCK) at 37° C., in an anaerobiosis jar (MERCK) in the presence of an oxygen fixer (AnaerocultA, MERCK).

A 10-microliter loop (NUNC) of bacteria is resuspended in 1 milliliter of sterile water. The bacteria are lyzed with 2 cycles of vigorous shaking, 20 seconds at 5000 rotations per minute in the presence of glass microbeads (0.5 mm in diameter, BIOSPEC PRODUCTS), and then addition of 0.15 ml of chloroform. The mixture is shaken for 30 minutes at 37° C., and the volume is made to 2 ml with sterile water at 4° C. The beta-galactosidase activity is then measured: starting with 0.2 ml of the cell suspension, 1.2 ml of 0.067M $NaH_2PO_4$ buffer, pH 6.8; 0.05 ml of L-cysteine (SIGMA) at t0 0.05 ml of O-nitrophenyl-beta-D-galactopyranoside (SIGMA) are added. The enzymatic reaction is stopped after 0, 2, 5 or 10 min, with 1 ml of 10% $Na_2CO_3$ buffer, and, after centrifugation of the reaction medium, a measurement of the OD at 400 nanometers is performed on the supernatant.

The galactosidase activities of the LbS parent strain and of the I-1968 mutant in accordance with the invention, measured as a function of time, are given in FIG. 1.

These results show that the β-galactosidase is totally inactive in the mutant in accordance with the invention.

EXAMPLE 2

Stability of the I-1968 Mutant of *L. Bulgaricus*

The stability of the I-1968 mutant was tested in media containing, as carbon sources, either a mixture of glucose and of lactose, or lactose only.

An I-1968 culture obtained on MRS medium containing glucose is subcultured on sterilized milk which is supplemented with yeast autolyzate (2 g/l) and which may or may not be supplemented with glucose (20 g/l). When a pH of 5.2 (coagulation of the milk) is reached, samples of each sub-culturing are taken, on which the capacity of the bacteria to ferment sugars, as well as the presence of β-galactosidase activity (X-gal plate assay: white colonies=β-galactosidase minus; blue colonies=β-galactosidase plus), and analyzed.

The results are given in Table 1 below.

TABLE I

| Medium | Milk + glucose (20 g/l) | Milk |
|---|---|---|
| Time to reach pH 5.2 | 6 h 00 | 20 h 00 |
| Fermentation of sugars | glucose, fructose, mannose | lactose, glucose, fructose, mannose |
| X-gal plate assay | 100% white colonies | 20% white colonies 80% blue colonies |

These results show that, in the presence of glucose, the I-1968 strain does not revert toward a strain capable of using lactose. Conversely, in a medium containing lactose as the only carbon source, rapid reversion of the I-1968 strain toward the original state is observed.

EXAMPLE 3

Acidification, Postacidification and Survival Properties of the I-1968 Variant of *L. Bulgaricus* in Symbiosis with *S. Thermophilus*: the Case of a Method for Manufacturing a Set Yogurt (Fermentation in a Ventilated Oven)

Yogurt ferments are prepared combining the I-1968 strain in accordance with the invention with various industrial strains of *S. thermophilus* (the strains of *S. thermophilus* used are hereafter termed ST1, ST2 and ST3).

By way of comparison, the ferments are prepared combining the LbS parent strain and the same strains of *S. thermophilus*.

For preparing the ferments, the strains are seeded separately and at 1% on the following composition:

Composition for 1 Liter:

135 g of skimmed milk powder 2 g of yeast autolyzate 920 ml of distilled water 20 g of glucose (for the I-1968 strain only)

| Hydration: | 10 min |
|---|---|
| Pasteurization: | 30 min at 95° C. |

The milk is then cooled to 44° C. and inoculated, and then incubated at 44° C. until an acidity of 85° D (degrees Dornic) for the *streptococci* and of 80° D for the *lactobacilli* is obtained.

The cultures are then cooled so as to obtain a ferment consisting of 80% *Streptococcus thermophilus* and of 20% *Lactobacillus bulgaricus*.

The ferments thus obtained are used to inoculate the following preparation:

Composition for 1 Liter:

99% of milk 0, 1, or 2 g/l of glucose

| Hydration: | 10 min |
|---|---|
| Pasteurization: | 10 min at 95° C. |

The milk is then cooled to 44° C. and inoculated at 1%.

For each experiment, the composition of the ferment and the amount of glucose added are given in Table II below:

TABLE II

| Experiment | Glucose g/l | Strains | Percentage |
|---|---|---|---|
| 1 | 0 | ST 3 | 64% |
|  |  | ST 2 | 16% |
|  |  | LbS | 20% |
| 2 | 0 | ST 3 | 64% |
|  |  | ST 2 | 16% |
|  |  | I-1968 | 20% |
| 3 | 1 | ST 3 | 64% |
|  |  | ST 2 | 16% |
|  |  | I-1968 | 20% |
| 4 | 0 | ST 1 | 80% |
|  |  | LbS | 20% |
| 5 | 0 | ST 1 | 80% |
|  |  | I-1968 | 20% |
| 6 | 2 | ST 1 | 80% |
|  |  | I-1968 | 20% |

After inoculation, the milk is distributed into round-bottomed flasks and incubated at a temperature of 44° C. The acidification profile is monitored during the incubation. The products are uncurdled at pH 4.6 by cooling in a cold unit (16 hours at 4° C.).

The products are then subjected to a conservation test at 10° C. In this test, the pH and Dornic acidity are measured after 1, 14, 21 and 28 days of conservation.

The acidification results (time to reach a pH of 4.6 and pH value at 24 h) are given in Table III below:

TABLE III

| Experiment | Time to reach pH 4.6 (min) | Time to reach pH 4.5 (min) | pH at 24 h |
|---|---|---|---|
| 1 | 215 | 236 | 3.67 |
| 2 | 550 | 778 | 4.33 |
| 3 | 416 | 507 | 4.26 |
| 4 | 225 | 241 | 3.67 |
| 5 | 660 | >1500 | 4.54 |
| 6 | 390 | 465 | 4.35 |

The results of the conservation test at 10° C. (monitoring of the pH and of the Dornic acidity) and the survival test (*S. thermophilus* and *L. bulgaricus* populations) at 28 days are given in Table IV below:

TABLE IV

| Experiment | Storage time (days) | pH | Dornic acidity | Streptococcus thermophilus cells/ml | Lactobacillus bulgaricus cells/ml |
|---|---|---|---|---|---|
| 1 | 1 | 4.41 | 101 | 7.25E + 08 | 3.35E + 08 |
| 1 | 14 | 3.98 | 140 | ND | ND |
| 1 | 21 | 3.95 | 145 | ND | ND |
| 1 | 28 | 3.9 | 148 | 7.35E + 08 | 3.30E + 08 |
| 2 | 1 | 4.5 | 93 | 5.60E + 08 | 2.90E + 07 |
| 2 | 14 | 4.23 | 110 | Nd | ND |
| 2 | 21 | 4.18 | 112 | ND | ND |
| 2 | 28 | 4.19 | 114 | 5.6SE + 08 | 1.87E + 07 |
| 3 | 1 | 4.49 | 96 | 6.90E + 08 | 7.45E + 07 |
| 3 | 14 | 4.14 | 115 | ND | ND |
| 3 | 21 | 4.15 | 117 | ND | ND |
| 3 | 28 | 4.15 | 120 | 5.65E + 08 | 6.30E + 07 |
| 4 | 1 | 4.39 | 105 | 6.30E + 07 | 4.40E + 08 |
| 4 | 14 | 3.91 | 145 | &D | ND |
| 4 | 21 | 3.9 | 151 | ND | ND |
| 4 | 28 | 3.85 | 157 | 4.70E + 08 | 6.30E + 08 |
| 5 | 1 | 4.6 | 85 | 9.05E + 08 | 6.70E + 07 |
| 5 | 14 | 4.58 | 80 | ND | ND |
| 5 | 21 | 4.53 | 80 | ND | ND |
| 5 | 28 | 4.61 | 79 | 9.40E + 08 | 7.00E + 07 |
| 6 | 1 | 4.51 | 89 | 1.05E + 09 | 1.96E + 08 |
| 6 | 14 | 4.38 | 90 | ND | ND |
| 6 | 21 | 4.39 | 96 | ND | ND |
| 6 | 28 | 4.42 | 90 | 1.62E + 09 | 1.91E + 08 |

ND = Not Determined

These results show that the yogurts produced using the symbioses combining the I-1968 strain with one or two strains of *S. thermophilus* show extremely reduced postacidification with respect to the same symbioses with the LbS parent strain, while at the same time conserving an abundant population at the end of fermentation and good survival for 28 days at 10° C.

Stopping the acidification and maintaining the pH at around 4.6 to 4.5 for at least 24 hours at 44° C. makes it possible, in the context of manufacturing stirred yogurt, to reduce or even eliminate the phase of cooling in a tank, which is conventionally used.

What is claimed is:

1. A mutant strain of *L. bulgaricus* which was deposited on Jan. 14, 1998 with the CNCM under the number I-1968, said strain lacking β-galactosidase activity and carrying a non-sense mutation in at least one of the coding sequences of the lactose operon.

2. A mutant strain of *L. bulgaricus* deposited on Jan. 14, 1998 with the CNCM under the number I-1968.

3. A lactic ferment which comprises at least one strain of *L. bulgaricus* as claimed in claim 2.

4. The lactic ferment as claimed in claim 3, wherein said strain of *L. bulgaricus* is combined with at least one strain of *S. thermophilus*.

5. A method for preparing a fermented dairy product, which comprises a step wherein milk is fermented using a lactic ferment comprising at least one strain of *L. bulgaricus* as claimed in claim 2, in the presence of at least one sugar which can be assimilated by said strain.

6. The method as claimed in claim 5, wherein said sugar which can be assimilated is glucose.

7. The method as claimed in claim 5, wherein the arrest of fermentation is carried out without cooling of said dairy product.

8. A fermented dairy product obtained by the method as claimed in claim 5.

9. The fermented dairy product as claimed in claim 8 wherein said product is a yogurt.

* * * * *

SEQUENCE LISTING

```
<160> NUMBER OF SEQ ID NOS: 3

<210> SEQ ID NO 1
<211> LENGTH: 5059
<212> TYPE: DNA
<213> ORGANISM: Lactobacillus bulgaricus
<220> FEATURE:
<221> NAME/KEY: CDS
<222> LOCATION: (122)..(1873)
<221> NAME/KEY: CDS
<222> LOCATION: (1877)..(4519)

<400> SEQUENCE: 1
gcttgtctca cgcttgtcgt acgcggccgg tgcctttggc aacgacgtct tctacgcgac      60
tctgtcaacc tactttatcg tcttcgtcac caccacctc tttaatgccg gtgaccacaa     120 g atg atc ttt atc atc acc aac ttg atc acc gcc atc cgg atc ggg gaa    169
  Met Ile Phe Ile Ile Thr Asn Leu Ile Thr Ala Ile Arg Ile Gly Glu
  1               5                   10                  15 gtc ctg ctc gac ccc ttg atc ggt aac gcc atc gac cgg acc gaa agc      217
Val Leu Leu Asp Pro Leu Ile Gly Asn Ala Ile Asp Arg Thr Glu Ser
             20                  25                  30 cgg tgg ggg aag ttc aag ccc tgg gtt gtg ggc ggg ggg atc atc agc      265
Arg Trp Gly Lys Phe Lys Pro Trp Val Val Gly Gly Gly Ile Ile Ser
         35                  40                  45 tca tta gcc ctc tta gcc ctc ttt acc gac ttt ggc ggc att aac caa      313
Ser Leu Ala Leu Leu Ala Leu Phe Thr Asp Phe Gly Gly Ile Asn Gln
     50                  55                  60 agc aac ccc gtt gtt tac tta gta atc ttc ggt att gtt tac ttg att      361
```

```
                                                              -continued

Ser Asn Pro Val Val Tyr Leu Val Ile Phe Gly Ile Val Tyr Leu Ile
 65              70                  75                  80 atg gat atc ttc tac tca ttt aaa gac act ggc ttc tgg gcc atg atc           409
Met Asp Ile Phe Tyr Ser Phe Lys Asp Thr Gly Phe Trp Ala Met Ile
                    85                  90                  95 ccg gcc ttg tcc ctg gat tcc cgg gaa aga gag aag acc tcc acc ttc           457
Pro Ala Leu Ser Leu Asp Ser Arg Glu Arg Glu Lys Thr Ser Thr Phe
                100                 105                 110 gcc aga gtc ggc tcc acc atc ggg gcc aac ctg gtc ggg gta gtc atc           505
Ala Arg Val Gly Ser Thr Ile Gly Ala Asn Leu Val Gly Val Val Ile
            115                 120                 125 acc cca atc atc ctc ttc ttc tcg gcc agc aag gcc aac ccc aac ggg           553
Thr Pro Ile Ile Leu Phe Phe Ser Ala Ser Lys Ala Asn Pro Asn Gly
        130                 135                 140 gat aag cag ggc tgg ttc ttc ttt gcc ttg atc gtg gcc att gtc ggc           601
Asp Lys Gln Gly Trp Phe Phe Phe Ala Leu Ile Val Ala Ile Val Gly
145                 150                 155                 160 atc ttg acc tca att acc gtt ggt ctt ggt act cac gaa gta aaa tcc           649
Ile Leu Thr Ser Ile Thr Val Gly Leu Gly Thr His Glu Val Lys Ser
                165                 170                 175 gcc ctg cgg gaa agc aat gaa aag acc act ttg aag cag gtc ttt aag           697
Ala Leu Arg Glu Ser Asn Glu Lys Thr Thr Leu Lys Gln Val Phe Lys
                180                 185                 190 gtc ctg ggg caa aac gac cag ctc ctc tgg ctg gcc ttt gcc tac tgg           745
Val Leu Gly Gln Asn Asp Gln Leu Leu Trp Leu Ala Phe Ala Tyr Trp
            195                 200                 205 ttt tac ggc ctg ggt atc aac acc ctg aac gct ctg caa ctt tac tac           793
Phe Tyr Gly Leu Gly Ile Asn Thr Leu Asn Ala Leu Gln Leu Tyr Tyr
        210                 215                 220 ttc tca tac atc tta ggc gat gcc cgc ggc tac agc ctg ctt tac acc           841
Phe Ser Tyr Ile Leu Gly Asp Ala Arg Gly Tyr Ser Leu Leu Tyr Thr
225                 230                 235                 240 atc aac acc ttt gtc ggt tta atc tct gca tcc ttc ttc cca tca ctg           889
Ile Asn Thr Phe Val Gly Leu Ile Ser Ala Ser Phe Phe Pro Ser Leu
                245                 250                 255 gcc aag aag ttc aac aga aat cgc ctc ttc tac gcc tgc atc gcg gtg           937
Ala Lys Lys Phe Asn Arg Asn Arg Leu Phe Tyr Ala Cys Ile Ala Val
                260                 265                 270 atg ctg tta ggg atc ggg gtc ttc tcc gtg gcc agc ggt tct ctg gcc           985
Met Leu Leu Gly Ile Gly Val Phe Ser Val Ala Ser Gly Ser Leu Ala
            275                 280                 285 ctg tcc ctt gtt ggg gca gaa ttc ttc ttt att ccg cag cct ctg gcc          1033
Leu Ser Leu Val Gly Ala Glu Phe Phe Phe Ile Pro Gln Pro Leu Ala
        290                 295                 300 ttc ctg gtc gtt ttg atg atc atc tct gac gct gtt gaa tac ggc cag          1081
Phe Leu Val Val Leu Met Ile Ile Ser Asp Ala Val Glu Tyr Gly Gln
305                 310                 315                 320 ctg aaa act ggc cac aga gac gaa gct ttg acc ctg tct gtc cgg cca          1129
Leu Lys Thr Gly His Arg Asp Glu Ala Leu Thr Leu Ser Val Arg Pro
                325                 330                 335 ttg gtc gat aag ctg ggc ggg gcc ttg tcc aac tgg ttt gtt tcc ttg          1177
Leu Val Asp Lys Leu Gly Gly Ala Leu Ser Asn Trp Phe Val Ser Leu
                340                 345                 350 att gcc tta act gcc ggc atg acc act ggg gcg act gcc tca aca att          1225
Ile Ala Leu Thr Ala Gly Met Thr Thr Gly Ala Thr Ala Ser Thr Ile
            355                 360                 365 aca gct cat ggc cag atg gtc ttc aag tta gct atg ttt gcc tta ccg          1273
Thr Ala His Gly Gln Met Val Phe Lys Leu Ala Met Phe Ala Leu Pro
        370                 375                 380
```

-continued

| | | | | | | | | | | | | | | | | |
|---|---|---|---|---|---|---|---|---|---|---|---|---|---|---|---|---|
| gca | gtc | atg | ctc | ttg | atc | gct | gtt | tct | att | ttc | gcc | aaa | aag | gtc | ttc | 1321 |
| Ala | Val | Met | Leu | Leu | Ile | Ala | Val | Ser | Ile | Phe | Ala | Lys | Lys | Val | Phe | |
| 385 | | | | 390 | | | | | 395 | | | | | 400 | | |
| ttg | act | gaa | gaa | aag | cac | gcg | gaa | atc | gtc | gac | cag | ctg | gaa | act | caa | 1369 |
| Leu | Thr | Glu | Glu | Lys | His | Ala | Glu | Ile | Val | Asp | Gln | Leu | Glu | Thr | Gln | |
| | | | | 405 | | | | | 410 | | | | | 415 | | |
| ttc | agc | caa | agc | cat | gcc | caa | aag | ccg | gcg | caa | gct | gaa | agc | ttc | act | 1417 |
| Phe | Ser | Gln | Ser | His | Ala | Gln | Lys | Pro | Ala | Gln | Ala | Glu | Ser | Phe | Thr | |
| | | | 420 | | | | | 425 | | | | | 430 | | | |
| ttg | gcc | agc | cca | gtc | tcc | gga | caa | tta | atg | aac | ctg | gac | atg | gtt | gac | 1465 |
| Leu | Ala | Ser | Pro | Val | Ser | Gly | Gln | Leu | Met | Asn | Leu | Asp | Met | Val | Asp | |
| | | | 435 | | | | | 440 | | | | | 445 | | | |
| gac | ccg | gtc | ttt | gcc | gac | aaa | aag | tta | ggc | gac | ggc | ttt | gcc | ctg | gtg | 1513 |
| Asp | Pro | Val | Phe | Ala | Asp | Lys | Lys | Leu | Gly | Asp | Gly | Phe | Ala | Leu | Val | |
| | 450 | | | | | 455 | | | | | 460 | | | | | |
| cca | gca | gac | ggt | aag | gtc | tac | gcg | cca | ttt | gcc | ggt | act | gtc | cgc | cag | 1561 |
| Pro | Ala | Asp | Gly | Lys | Val | Tyr | Ala | Pro | Phe | Ala | Gly | Thr | Val | Arg | Gln | |
| 465 | | | | 470 | | | | | 475 | | | | | 480 | | |
| ctg | gcc | aag | acc | cgg | cac | tcg | atc | gtc | ctg | gaa | aat | gaa | cat | ggg | gtc | 1609 |
| Leu | Ala | Lys | Thr | Arg | His | Ser | Ile | Val | Leu | Glu | Asn | Glu | His | Gly | Val | |
| | | | | 485 | | | | | 490 | | | | | 495 | | |
| ttg | gtc | ttg | att | cac | ctt | ggc | ctg | ggc | acg | gtc | aaa | tta | aac | ggg | act | 1657 |
| Leu | Val | Leu | Ile | His | Leu | Gly | Leu | Gly | Thr | Val | Lys | Leu | Asn | Gly | Thr | |
| | | | | 500 | | | | | 505 | | | | | 510 | | |
| ggc | ttt | gtc | agc | tat | gtt | gaa | gag | ggc | agc | cag | gta | gaa | gcc | ggc | cag | 1705 |
| Gly | Phe | Val | Ser | Tyr | Val | Glu | Glu | Gly | Ser | Gln | Val | Glu | Ala | Gly | Gln | |
| | | | 515 | | | | | 520 | | | | | 525 | | | |
| cag | atc | ctg | gaa | ttc | tgg | gac | ccg | gcg | atc | aag | cag | gcc | aag | ctg | gac | 1753 |
| Gln | Ile | Leu | Glu | Phe | Trp | Asp | Pro | Ala | Ile | Lys | Gln | Ala | Lys | Leu | Asp | |
| | 530 | | | | | 535 | | | | | 540 | | | | | |
| gac | acg | gta | atc | gtg | acc | gtc | atc | aac | agc | gaa | act | ttc | gca | aat | agc | 1801 |
| Asp | Thr | Val | Ile | Val | Thr | Val | Ile | Asn | Ser | Glu | Thr | Phe | Ala | Asn | Ser | |
| 545 | | | | 550 | | | | | 555 | | | | | 560 | | |
| cag | atg | ctc | ttg | ccg | atc | ggc | cac | agc | gtc | caa | gcc | ctg | gat | gat | gta | 1849 |
| Gln | Met | Leu | Leu | Pro | Ile | Gly | His | Ser | Val | Gln | Ala | Leu | Asp | Asp | Val | |
| | | | | 565 | | | | | 570 | | | | | 575 | | |
| ttc | aag | tta | gaa | ggg | aag | aat | tag | aaa | atg | agc | aat | aag | tta | gta | aaa | 1897 |
| Phe | Lys | Leu | Glu | Gly | Lys | Asn | | | Met | Ser | Asn | Lys | Leu | Val | Lys | |
| | | | 580 | | | | | | | 585 | | | | | 590 | |
| gaa | aaa | aga | gtt | gac | cag | gca | gac | ttg | gcc | tgg | ctg | act | gac | ccg | gaa | 1945 |
| Glu | Lys | Arg | Val | Asp | Gln | Ala | Asp | Leu | Ala | Trp | Leu | Thr | Asp | Pro | Glu | |
| | | | 595 | | | | | 600 | | | | | 605 | | | |
| gtt | tac | gaa | gtc | aat | aca | att | ccc | ccg | cac | tcc | gac | cat | gag | tcc | ttc | 1993 |
| Val | Tyr | Glu | Val | Asn | Thr | Ile | Pro | Pro | His | Ser | Asp | His | Glu | Ser | Phe | |
| | | 610 | | | | | 615 | | | | | 620 | | | | |
| caa | agc | cag | gaa | gaa | ctg | gag | gag | ggc | aag | tcc | agt | tta | gtg | cag | tcc | 2041 |
| Gln | Ser | Gln | Glu | Glu | Leu | Glu | Glu | Gly | Lys | Ser | Ser | Leu | Val | Gln | Ser | |
| 625 | | | | 630 | | | | | 635 | | | | | | | |
| ctg | gac | ggg | gac | tgg | ctg | att | gac | tac | gct | gaa | aac | ggc | cag | gga | cca | 2089 |
| Leu | Asp | Gly | Asp | Trp | Leu | Ile | Asp | Tyr | Ala | Glu | Asn | Gly | Gln | Gly | Pro | |
| 640 | | | | 645 | | | | | 650 | | | | | 655 | | |
| gtc | aac | ttc | tat | gca | gaa | gac | ttt | gac | gat | agc | aat | ttt | aag | tca | gtc | 2137 |
| Val | Asn | Phe | Tyr | Ala | Glu | Asp | Phe | Asp | Asp | Ser | Asn | Phe | Lys | Ser | Val | |
| | | | 660 | | | | | 665 | | | | | 670 | | | |
| aaa | gta | ccc | ggc | aac | ctg | gaa | ctg | caa | ggc | ttt | ggc | cag | ccc | cag | tat | 2185 |
| Lys | Val | Pro | Gly | Asn | Leu | Glu | Leu | Gln | Gly | Phe | Gly | Gln | Pro | Gln | Tyr | |
| | | | 675 | | | | | 680 | | | | | 685 | | | |
| gtc | aac | gtc | caa | tat | cca | tgg | gac | ggc | agt | gag | gag | att | ttc | ccg | ccc | 2233 |
| Val | Asn | Val | Gln | Tyr | Pro | Trp | Asp | Gly | Ser | Glu | Glu | Ile | Phe | Pro | Pro | |
| | | 690 | | | | | 695 | | | | | 700 | | | | |

```
caa att cca agc aaa aat ccg ctc gct tct tat gtc aga tac ttt gac       2281
Gln Ile Pro Ser Lys Asn Pro Leu Ala Ser Tyr Val Arg Tyr Phe Asp
705                 710                 715 ctg gat gaa gct ttc tgg gac aag gaa gtc agc ttg aag ttt gac ggg       2329
Leu Asp Glu Ala Phe Trp Asp Lys Glu Val Ser Leu Lys Phe Asp Gly
720                 725                 730                 735 gcg gca aca gcc atc tat gtc tgg ctg aac ggc cac ttc gtc ggc tac       2377
Ala Ala Thr Ala Ile Tyr Val Trp Leu Asn Gly His Phe Val Gly Tyr
                740                 745                 750 ggg gaa gac tcc ttt acc cca agc gag ttt atg gtt acc aag ttc ctc       2425
Gly Glu Asp Ser Phe Thr Pro Ser Glu Phe Met Val Thr Lys Phe Leu
            755                 760                 765 aag aaa gaa aat aac cgc ctg gca gtg gct ctc tac aag tat tct tcc       2473
Lys Lys Glu Asn Asn Arg Leu Ala Val Ala Leu Tyr Lys Tyr Ser Ser
        770                 775                 780 gcc tcc tgg ctg gaa gac cag gac ttc tgg cgc atg tct ggt ttg ttc       2521
Ala Ser Trp Leu Glu Asp Gln Asp Phe Trp Arg Met Ser Gly Leu Phe
785                 790                 795 aga tca gtg act ctt cag gcc aag ccg cgt ctg cac ttg gag gac ctt       2569
Arg Ser Val Thr Leu Gln Ala Lys Pro Arg Leu His Leu Glu Asp Leu
800                 805                 810                 815 aag ctt acg gcc agc ttg acc gat aac tac caa aaa gga aag ctg gaa       2617
Lys Leu Thr Ala Ser Leu Thr Asp Asn Tyr Gln Lys Gly Lys Leu Glu
                820                 825                 830 gtc gaa gcc aat att gcc tac cgc ttg cca aat gcc agc ttt aag ctg       2665
Val Glu Ala Asn Ile Ala Tyr Arg Leu Pro Asn Ala Ser Phe Lys Leu
            835                 840                 845 gaa gtg cgg gat agt gaa ggt gac ttg gtt gct gaa aag ctg ggc cca       2713
Glu Val Arg Asp Ser Glu Gly Asp Leu Val Ala Glu Lys Leu Gly Pro
        850                 855                 860 atc aga agc gag cag ctg gaa ttc act ctg gct gat ttg cca gta gct       2761
Ile Arg Ser Glu Gln Leu Glu Phe Thr Leu Ala Asp Leu Pro Val Ala
865                 870                 875 gcc tgg agc gcg gaa aag cct aac ctt tac cag gtc cgc ctg tat tta       2809
Ala Trp Ser Ala Glu Lys Pro Asn Leu Tyr Gln Val Arg Leu Tyr Leu
880                 885                 890                 895 tac cag gca ggc agc ctc tta gag gtt agc cgg cag gaa gtg ggt ttc       2857
Tyr Gln Ala Gly Ser Leu Leu Glu Val Ser Arg Gln Glu Val Gly Phe
                900                 905                 910 cgc aac ttt gaa cta aaa gac ggg att atg tac ctt aac ggc cag cgg       2905
Arg Asn Phe Glu Leu Lys Asp Gly Ile Met Tyr Leu Asn Gly Gln Arg
            915                 920                 925 atc gtc ttc aag ggg gcc aac cgg cac gaa ttt gac agt aag ttg ggc       2953
Ile Val Phe Lys Gly Ala Asn Arg His Glu Phe Asp Ser Lys Leu Gly
        930                 935                 940 cgg gct atc aca gaa gag gat atg atc tgg gat atc aag acc atg aag       3001
Arg Ala Ile Thr Glu Glu Asp Met Ile Trp Asp Ile Lys Thr Met Lys
945                 950                 955 cga agc aac atc aat gct gtc cgc tgc tct cac tac ccg aac cag tcc       3049
Arg Ser Asn Ile Asn Ala Val Arg Cys Ser His Tyr Pro Asn Gln Ser
960                 965                 970                 975 ctc ttt tac cgg ctc tgt gac aag tac ggc ctt tac gtc att gat gaa       3097
Leu Phe Tyr Arg Leu Cys Asp Lys Tyr Gly Leu Tyr Val Ile Asp Glu
                980                 985                 990 gct aac ctg gaa agc cac ggc acc tgg gaa aaa gtg ggg ggg cac gaa       3145
Ala Asn Leu Glu Ser His Gly Thr Trp Glu Lys Val Gly Gly His Glu
            995                 1000                1005 gat cct agc ttc aat gtt cca ggc gat gac cag cat tgg ctg gga gcc       3193
Asp Pro Ser Phe Asn Val Pro Gly Asp Asp Gln His Trp Leu Gly Ala
```

-continued

| | |
|---|---|
| agc tta tcc cgg gtg aag aac atg atg gct cgg gac aag aac cat gct<br>Ser Leu Ser Arg Val Lys Asn Met Met Ala Arg Asp Lys Asn His Ala<br>  1025                    1030                    1035 | 3241 |
| tca atc ctg atc tgg tct tta ggc aat gag tct tac gcc ggc act gtc<br>Ser Ile Leu Ile Trp Ser Leu Gly Asn Glu Ser Tyr Ala Gly Thr Val<br>1040                  1045                  1050                  1055 | 3289 |
| ttt gcc caa atg gct gat tac gtc cgg aag gct gat ccg acc cgg gtt<br>Phe Ala Gln Met Ala Asp Tyr Val Arg Lys Ala Asp Pro Thr Arg Val<br>                  1060                  1065                  1070 | 3337 |
| cag cac tat gaa ggg gtg acc cac aac cgg aag ttt gac gac gcc acc<br>Gln His Tyr Glu Gly Val Thr His Asn Arg Lys Phe Asp Asp Ala Thr<br>            1075                    1080                  1085 | 3385 |
| cag att gaa agc cgg atg tat gct ccg gcc aag gta att gaa gaa tac<br>Gln Ile Glu Ser Arg Met Tyr Ala Pro Ala Lys Val Ile Glu Glu Tyr<br>                  1090                  1095                  1100 | 3433 |
| ttg acc aat aaa cca gcc aag cca ttt atc tca gtt gaa tac gct cac<br>Leu Thr Asn Lys Pro Ala Lys Pro Phe Ile Ser Val Glu Tyr Ala His<br>    1105                    1110                    1115 | 3481 |
| gcc atg ggc aac tcc gtc ggt gac ctg gcc gcc tac acg gcc ctg gaa<br>Ala Met Gly Asn Ser Val Gly Asp Leu Ala Ala Tyr Thr Ala Leu Glu<br>1120                  1125                  1130                  1135 | 3529 |
| aaa tac ccc cac tac cag ggc ggc ttc atc tgg gac tgg att gac caa<br>Lys Tyr Pro His Tyr Gln Gly Gly Phe Ile Trp Asp Trp Ile Asp Gln<br>                  1140                  1145                  1150 | 3577 |
| gga ctg gaa aaa gac ggg cac ctg ctt tat ggg ggc gac ttc gat gac<br>Gly Leu Glu Lys Asp Gly His Leu Leu Tyr Gly Gly Asp Phe Asp Asp<br>            1155                    1160                  1165 | 3625 |
| cgg cca acc gac tat gaa ttc tgc ggg aac ggc ctg gtc ttt gct gac<br>Arg Pro Thr Asp Tyr Glu Phe Cys Gly Asn Gly Leu Val Phe Ala Asp<br>        1170                    1175                    1180 | 3673 |
| cgg act gaa tcg ccg aaa ctg gct aat gtc aag gcc ctt tac gcc aac<br>Arg Thr Glu Ser Pro Lys Leu Ala Asn Val Lys Ala Leu Tyr Ala Asn<br>1185                  1190                  1195 | 3721 |
| ctt aag tta gaa gta aaa gat ggg cag ctc ttc ctc aaa aac gac aat<br>Leu Lys Leu Glu Val Lys Asp Gly Gln Leu Phe Leu Lys Asn Asp Asn<br>1200                  1205                  1210                  1215 | 3769 |
| tta ttt acc aac agc tca tct tac tac ttc ttg act agt ctt ttg gtc<br>Leu Phe Thr Asn Ser Ser Ser Tyr Tyr Phe Leu Thr Ser Leu Leu Val<br>                  1220                  1225                  1230 | 3817 |
| gat ggc aag ttg acc tac cag agc cgg cct ctg acc ttt ggc ctg gag<br>Asp Gly Lys Leu Thr Tyr Gln Ser Arg Pro Leu Thr Phe Gly Leu Glu<br>            1235                    1240                  1245 | 3865 |
| cct ggc gaa tcc ggg acc ttt gcc ctg cct tgg ccg gaa gtc gct gat<br>Pro Gly Glu Ser Gly Thr Phe Ala Leu Pro Trp Pro Glu Val Ala Asp<br>1250                  1255                  1260 | 3913 |
| gaa aaa gga gag gtc gtc tac cgg gta acg gcc cac tta aaa gaa gac<br>Glu Lys Gly Glu Val Val Tyr Arg Val Thr Ala His Leu Lys Glu Asp<br>                  1265                  1270                  1275 | 3961 |
| ttg cct tgg gcg gat gag ggc ttc act gtg gct gaa gca gaa gaa gta<br>Leu Pro Trp Ala Asp Glu Gly Phe Thr Val Ala Glu Ala Glu Glu Val<br>1280                  1285                  1290                  1295 | 4009 |
| gct caa aag ctg ccg gaa ttt aag ccg gaa ggg cgg cca gat tta gtt<br>Ala Gln Lys Leu Pro Glu Phe Lys Pro Glu Gly Arg Pro Asp Leu Val<br>                  1300                  1305                  1310 | 4057 |
| gat tcc gac tac aac cta ggc ctg aaa gga aat aac ttc caa att ctc<br>Asp Ser Asp Tyr Asn Leu Gly Leu Lys Gly Asn Asn Phe Gln Ile Leu<br>            1315                    1320                  1325 | 4105 |
| ttc tcc aag gtc aag ggc tgg ccg gtt tcc ctc aag tat gcc ggt agg | 4153 |

```
Phe Ser Lys Val Lys Gly Trp Pro Val Ser Leu Lys Tyr Ala Gly Arg
    1330                1335                1340 gaa tac ttg aag cgg ctg ccg gaa ttt acc ttc tgg cgg gcc ctg acg          4201
Glu Tyr Leu Lys Arg Leu Pro Glu Phe Thr Phe Trp Arg Ala Leu Thr
    1345                1350                1355 gac aac gac cgg gga gct ggt tac ggc tat gat ctg gcc cgg tgg gaa          4249
Asp Asn Asp Arg Gly Ala Gly Tyr Gly Tyr Asp Leu Ala Arg Trp Glu
1360                1365                1370                1375 aat gcc ggc aag tat gcc cgc ttg aaa gac atc agc tgc gag gtc aag          4297
Asn Ala Gly Lys Tyr Ala Arg Leu Lys Asp Ile Ser Cys Glu Val Lys
        1380                1385                1390 gaa gac tcc gtt ttg gtc aag act gcc ttt acg ttg cct gtc gcc tta          4345
Glu Asp Ser Val Leu Val Lys Thr Ala Phe Thr Leu Pro Val Ala Leu
            1395                1400                1405 aag ggt gat tta act gtg acc tat gaa gtc gat gga cgg ggc aag att          4393
Lys Gly Asp Leu Thr Val Thr Tyr Glu Val Asp Gly Arg Gly Lys Ile
        1410                1415                1420 gct gta aca gct gac ttc cca ggc gcg gaa gaa gcc ggt ctc ttg cca          4441
Ala Val Thr Ala Asp Phe Pro Gly Ala Glu Glu Ala Gly Leu Leu Pro
    1425                1430                1435 gcc ttt ggc ttg aac ctg gcc ctg cca aaa gaa ctg acc gat tac cgc          4489
Ala Phe Gly Leu Asn Leu Ala Leu Pro Lys Glu Leu Thr Asp Tyr Arg
1440                1445                1450                1455 tac tat ggt ctg gga cct aat gag agc taa ccagaccgct tggaaggtaa            4539
Tyr Tyr Gly Leu Gly Pro Asn Glu Ser
        1460                1465 ttacctgggc atctaccagg gagcggtaaa aaagaacttt agcccatacc tgcgtccgca        4599
ggaaacgggc aaccggagca aggttcgctg gtaccagctc tttgatgaaa agggcggctt        4659
ggaatttacg gccaatgggg cagacttgaa cttgtctgct ttgccatatt ctgccgccca        4719
aattgaagca gcggaccacg cttttgaact gactaacaat tacacttggg ttagagcctt        4779
aagcgcccag atgggggtcg gcggggatga ctcctggggg cagaaggtcc acccggaatt        4839
ctgcctggat gctcaaaaag cccgccagct ccgcctggtg attcagcccc ttttactaaa        4899
ataaatgcta caattgactt aacaggatga aattttagta aaagcaaagc gagtgaggaa        4959
gatggcaacg atcagagaag tgccaaggca gccggcgtgt cgctagcgac ggtttcccgc        5019
gtcttgaact atgaccagac cctgtcagtc aatgaggcaa                              5059
```

<210> SEQ ID NO 2
<211> LENGTH: 583
<212> TYPE: PRT
<213> ORGANISM: Lactobacillus bulgaricus

<400> SEQUENCE: 2

```
Met Ile Phe Ile Ile Thr Asn Leu Ile Thr Ala Ile Arg Ile Gly Glu
1               5                   10                  15

Val Leu Leu Asp Pro Leu Ile Gly Asn Ala Ile Asp Arg Thr Glu Ser
            20                  25                  30

Arg Trp Gly Lys Phe Lys Pro Trp Val Gly Gly Ile Ile Ser
        35                  40                  45

Ser Leu Ala Leu Leu Ala Leu Phe Thr Asp Phe Gly Ile Asn Gln
    50                  55                  60

Ser Asn Pro Val Val Tyr Leu Val Ile Phe Gly Ile Val Tyr Leu Ile
65                  70                  75                  80

Met Asp Ile Phe Tyr Ser Phe Lys Asp Thr Gly Phe Trp Ala Met Ile
            85                  90                  95
```

-continued

```
Pro Ala Leu Ser Leu Asp Ser Arg Glu Arg Glu Lys Thr Ser Thr Phe
            100                 105                 110
Ala Arg Val Gly Ser Thr Ile Gly Ala Asn Leu Val Gly Val Val Ile
            115                 120                 125
Thr Pro Ile Ile Leu Phe Phe Ser Ala Ser Lys Ala Asn Pro Asn Gly
        130                 135                 140
Asp Lys Gln Gly Trp Phe Phe Ala Leu Ile Val Ala Ile Val Gly
145                 150                 155                 160
Ile Leu Thr Ser Ile Thr Val Gly Leu Gly Thr His Glu Val Lys Ser
                165                 170                 175
Ala Leu Arg Glu Ser Asn Glu Lys Thr Thr Leu Lys Gln Val Phe Lys
            180                 185                 190
Val Leu Gly Gln Asn Asp Gln Leu Leu Trp Leu Ala Phe Ala Tyr Trp
            195                 200                 205
Phe Tyr Gly Leu Gly Ile Asn Thr Leu Asn Ala Leu Gln Leu Tyr Tyr
        210                 215                 220
Phe Ser Tyr Ile Leu Gly Asp Ala Arg Gly Tyr Ser Leu Leu Tyr Thr
225                 230                 235                 240
Ile Asn Thr Phe Val Gly Leu Ile Ser Ala Ser Phe Phe Pro Ser Leu
                245                 250                 255
Ala Lys Lys Phe Asn Arg Asn Arg Leu Phe Tyr Ala Cys Ile Ala Val
            260                 265                 270
Met Leu Leu Gly Ile Gly Val Phe Ser Val Ala Ser Gly Ser Leu Ala
        275                 280                 285
Leu Ser Leu Val Gly Ala Glu Phe Phe Ile Pro Gln Pro Leu Ala
290                 295                 300
Phe Leu Val Val Leu Met Ile Ile Ser Asp Ala Val Glu Tyr Gly Gln
305                 310                 315                 320
Leu Lys Thr Gly His Arg Asp Glu Ala Leu Thr Leu Ser Val Arg Pro
                325                 330                 335
Leu Val Asp Lys Leu Gly Gly Ala Leu Ser Asn Trp Phe Val Ser Leu
            340                 345                 350
Ile Ala Leu Thr Ala Gly Met Thr Thr Gly Ala Thr Ala Ser Thr Ile
        355                 360                 365
Thr Ala His Gly Gln Met Val Phe Lys Leu Ala Met Phe Ala Leu Pro
            370                 375                 380
Ala Val Met Leu Leu Ile Ala Val Ser Ile Phe Ala Lys Lys Val Phe
385                 390                 395                 400
Leu Thr Glu Glu Lys His Ala Glu Ile Val Asp Gln Leu Glu Thr Gln
                405                 410                 415
Phe Ser Gln Ser His Ala Gln Lys Pro Ala Gln Ala Glu Ser Phe Thr
            420                 425                 430
Leu Ala Ser Pro Val Ser Gly Gln Leu Met Asn Leu Asp Met Val Asp
        435                 440                 445
Asp Pro Val Phe Ala Asp Lys Lys Leu Gly Asp Gly Phe Ala Leu Val
    450                 455                 460
Pro Ala Asp Gly Lys Val Tyr Ala Pro Phe Ala Gly Thr Val Arg Gln
465                 470                 475                 480
Leu Ala Lys Thr Arg His Ser Ile Val Leu Glu Asn Glu His Gly Val
                485                 490                 495
Leu Val Leu Ile His Leu Gly Leu Gly Thr Val Lys Leu Asn Gly Thr
            500                 505                 510
Gly Phe Val Ser Tyr Val Glu Glu Gly Ser Gln Val Glu Ala Gly Gln
```

```
                515                 520                 525
Gln Ile Leu Glu Phe Trp Asp Pro Ala Ile Lys Gln Ala Lys Leu Asp
        530                 535                 540

Asp Thr Val Ile Val Thr Val Ile Asn Ser Glu Thr Phe Ala Asn Ser
545                 550                 555                 560

Gln Met Leu Leu Pro Ile Gly His Ser Val Gln Ala Leu Asp Asp Val
                565                 570                 575

Phe Lys Leu Glu Gly Lys Asn
            580

<210> SEQ ID NO 3
<211> LENGTH: 880
<212> TYPE: PRT
<213> ORGANISM: Lactobacillus bulgaricus

<400> SEQUENCE: 3

Met Ser Asn Lys Leu Val Lys Glu Lys Arg Val Asp Gln Ala Asp Leu
  1               5                  10                  15

Ala Trp Leu Thr Asp Pro Glu Val Tyr Glu Val Asn Thr Ile Pro Pro
                 20                  25                  30

His Ser Asp His Glu Ser Phe Gln Ser Gln Glu Glu Leu Glu Glu Gly
             35                  40                  45

Lys Ser Ser Leu Val Gln Ser Leu Asp Gly Asp Trp Leu Ile Asp Tyr
         50                  55                  60

Ala Glu Asn Gly Gln Gly Pro Val Asn Phe Tyr Ala Glu Asp Phe Asp
 65                  70                  75                  80

Asp Ser Asn Phe Lys Ser Val Lys Val Pro Gly Asn Leu Glu Leu Gln
                 85                  90                  95

Gly Phe Gly Gln Pro Gln Tyr Val Asn Val Gln Tyr Pro Trp Asp Gly
                100                 105                 110

Ser Glu Glu Ile Phe Pro Pro Gln Ile Pro Ser Lys Asn Pro Leu Ala
            115                 120                 125

Ser Tyr Val Arg Tyr Phe Asp Leu Asp Glu Ala Phe Trp Asp Lys Glu
        130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
                180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
    210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Arg Ser Glu Gln Leu Glu Phe Thr
            275                 280                 285

Leu Ala Asp Leu Pro Val Ala Ala Trp Ser Ala Glu Lys Pro Asn Leu
        290                 295                 300
```

-continued

```
Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
            325                 330                 335

Met Tyr Leu Asn Gly Gln Arg Ile Val Phe Lys Gly Ala Asn Arg His
            340                 345                 350

Glu Phe Asp Ser Lys Leu Gly Arg Ala Ile Thr Glu Glu Asp Met Ile
            355                 360                 365

Trp Asp Ile Lys Thr Met Lys Arg Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
            420                 425                 430

Asp Gln His Trp Leu Gly Ala Ser Leu Ser Arg Val Lys Asn Met Met
            435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
            485                 490                 495

Arg Lys Phe Asp Asp Ala Thr Gln Ile Glu Ser Arg Met Tyr Ala Pro
            500                 505                 510

Ala Lys Val Ile Glu Glu Tyr Leu Thr Asn Lys Pro Ala Lys Pro Phe
            515                 520                 525

Ile Ser Val Glu Tyr Ala His Ala Met Gly Asn Ser Val Gly Asp Leu
530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
            565                 570                 575

Tyr Gly Gly Asp Phe Asp Asp Arg Pro Thr Asp Tyr Glu Phe Cys Gly
            580                 585                 590

Asn Gly Leu Val Phe Ala Asp Arg Thr Glu Ser Pro Lys Leu Ala Asn
            595                 600                 605

Val Lys Ala Leu Tyr Ala Asn Leu Lys Leu Glu Val Lys Asp Gly Gln
            610                 615                 620

Leu Phe Leu Lys Asn Asp Asn Leu Phe Thr Asn Ser Ser Ser Tyr Tyr
625                 630                 635                 640

Phe Leu Thr Ser Leu Leu Val Asp Gly Lys Leu Thr Tyr Gln Ser Arg
            645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
            675                 680                 685

Thr Ala His Leu Lys Glu Asp Leu Pro Trp Ala Asp Glu Gly Phe Thr
            690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
```

-continued

```
                725                     730                     735
Gly Asn Asn Phe Gln Ile Leu Phe Ser Lys Val Lys Gly Trp Pro Val
            740                     745                 750

Ser Leu Lys Tyr Ala Gly Arg Glu Tyr Leu Lys Arg Leu Pro Glu Phe
        755                     760              765

Thr Phe Trp Arg Ala Leu Thr Asp Asn Asp Arg Gly Ala Gly Tyr Gly
    770                     775              780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
            805                     810                 815

Phe Thr Leu Pro Val Ala Leu Lys Gly Asp Leu Thr Val Thr Tyr Glu
            820                     825              830

Val Asp Gly Arg Gly Lys Ile Ala Val Thr Ala Asp Phe Pro Gly Ala
        835                 840                 845

Glu Glu Ala Gly Leu Leu Pro Ala Phe Gly Leu Asn Leu Ala Leu Pro
    850                     855             860

Lys Glu Leu Thr Asp Tyr Arg Tyr Tyr Gly Leu Gly Pro Asn Glu Ser
865             870                 875                 880
```